US009670461B2

(12) United States Patent
Abe et al.

(10) Patent No.: US 9,670,461 B2
(45) Date of Patent: Jun. 6, 2017

(54) METHOD FOR UNDIFFERENTIATED GROWTH OF MESENCHYMAL STEM CELL AND METHOD FOR CONCENTRATION OF MESENCHYMAL STEM CELL (71) Applicants: Hiroyuki Abe, Fuchu (JP); Hiroaki Kawasaki, Tokyo (JP)

(72) Inventors: Hiroyuki Abe, Fuchu (JP); Hiroaki Kawasaki, Tokyo (JP)

( * ) Notice: Subject to any disclaimer, the term of this patent is extended or adjusted under 35 U.S.C. 154(b) by 0 days.

(21) Appl. No.: 14/342,975

(22) PCT Filed: Aug. 8, 2013

(86) PCT No.: PCT/JP2013/071559
§ 371 (c)(1),
(2) Date: Mar. 5, 2014

(87) PCT Pub. No.: WO2014/034407
PCT Pub. Date: Mar. 6, 2014

(65) Prior Publication Data
US 2014/0220686 A1 Aug. 7, 2014

(30) Foreign Application Priority Data
Aug. 31, 2012 (JP) .................................. 2012-192560

(51) Int. Cl.
*C12N 5/0775* (2010.01)
(52) U.S. Cl.
CPC ...... *C12N 5/0665* (2013.01); *C12N 2501/113* (2013.01); *C12N 2501/115* (2013.01); *C12N 2501/125* (2013.01); *C12N 2501/2303* (2013.01); *C12N 2501/2306* (2013.01); *C12N 2501/26* (2013.01); *C12N 2501/41* (2013.01)
(58) Field of Classification Search
None
See application file for complete search history.

(56) References Cited

U.S. PATENT DOCUMENTS

| 6,491,917 | B1 | 12/2002 | Thomas | |
| 2004/0229351 | A1* | 11/2004 | Rodriguez | G01N 33/5008 435/366 |
| 2005/0164380 | A1 | 7/2005 | Trisler | |
| 2006/0166362 | A1* | 7/2006 | Dezawa | C12N 5/0619 435/455 |
| 2006/0239980 | A1* | 10/2006 | Bernad Miana | C12N 5/0668 424/93.7 |
| 2007/0128722 | A1 | 6/2007 | Lin et al. | |
| 2008/0050347 | A1 | 2/2008 | Ichim | |
| 2008/0187518 | A1* | 8/2008 | Ogle | C12N 5/0654 424/93.7 |
| 2010/0047892 | A1* | 2/2010 | Laine | C08B 37/00 435/193 |
| 2010/0068806 | A1 | 3/2010 | Laine et al. | |
| 2010/0266558 | A1* | 10/2010 | Zipori | C12N 5/0663 424/93.7 |
| 2010/0291042 | A1 | 11/2010 | Crawford et al. | |
| 2012/0114614 | A1 | 5/2012 | Ratajczak et al. | |
| 2012/0315701 | A1 | 12/2012 | Sugiyama | |
| 2012/0329087 | A1 | 12/2012 | Tsuchiya | |

FOREIGN PATENT DOCUMENTS

| JP | 2007-535302 | 12/2007 |
| JP | 2009-213448 | 9/2009 |
| JP | 2011-219435 | 11/2011 |
| JP | 2012-120529 | 6/2012 |
| WO | 2006/054883 | 5/2006 |
| WO | 2008/087256 | 7/2008 |
| WO | 2008/104064 | 9/2008 |
| WO | 2011/040500 | 4/2011 |
| WO | 2011/111787 | 9/2011 |

OTHER PUBLICATIONS

Choi et al "Fibroblast Growth Factor-2 and -4 Promote the Proliferation of Bone Marrow Mesenchymal Stem Cells by the Activation of the Pl3K-Akt and ERK1/2 Signaling Pathways" (2008) Stem Cells and Development, vol. 17: 725-736.*
International Search Report of PCT/JP2013/071559 dated Sep. 10, 2013.
Yasutake, M. et al., Stem cell collection filter system for human placental/umbilical cord blood processing. Vox Sang., 80:101-105, 2001.
Basford, C. et al., The Cord Blood Separation League Table: a Comparison of the Major Clinical Grade Harvesting Techniques for Cord Blood Stem Cells. Inter. J. Stem Cells, 3:32-45, 2010.
Pittenger, M.F. et al., Multilineage Potential of Adult Human Mesenchymal Stem Cells Science, 284:143-147, 1999.
Seiji Furukawa et al., "Kato Kotsuzui Yurai Kan'yokei kansaibo no Collagen Gel . . . ", The Journal of the Japanese Orthopaedic Association, 2002, 76(8), pp. S1106.
Goshi Shiot A "Present and future views of . . . ", Regenative Medicine, 2009, 8(1), pp. 95-103, 12-14.
Manabu Kan'Yama et al., "Zogeshitsu Saisei ni Mukete no . . . ", Japan Prosthodontic Society . . . , 2004, 112th, pp. 48.
Kondo, T., et al., Sonic hedeghog and retinoic acid . . . , PNAS, 2005, 102(13, pp. 4789-4794).
Ito. T., et al., FGF-2 suppresses cellular senescence of . . . , Biochemical and Biophysical Research Communications, 2007,359, pp. 108-114.
Ahn, H.-J., et al., FGF2 stimulates the proliferation of . . . , FEBS Letters, 2009, 583, pp. 2922-2926.

(Continued)

*Primary Examiner* — Allison Fox
(74) *Attorney, Agent, or Firm* — Casimir Jones, S.C.

(57) ABSTRACT

A method in accordance with the present invention includes the steps of: concentrating cord blood-derived mesenchymal stem cells; and causing the mesenchymal stem cells thus concentrated to grow with use of a particular factor while maintaining undifferentiated state of the mesenchymal stem cells.

4 Claims, 4 Drawing Sheets (56) References Cited

OTHER PUBLICATIONS

Ito. T., et al., "FGF-2 increases osteogenic . . . ",Cytotechnology, 2008, 56, pp. 1-7.
Warzecha J., et al., Sonic hedgehog protein promotes . . . , J. Orthop. Sci., 2006, 11, pp. 491-496.
Cetinalp, P. D., et al., "Study on the Immuno-Suppressive . . . ", Haematologica the hematology journal, 2010, 95(s2), pp. 652.
Saturi A T., et al., Optimizing the Isolation of . . . , Haematologica the hematology journal, 2010, 95(s2), pp. 664.
Woodside S. M., et al., Fully Automated Magnetic Labeling and . . . ,(online), Blood (Ash Annual Meeting Abstracts), 2005, 106, Abstract 1074.
Baddoo M., et al., Characterization of Mesenchymal Stem Cells . . . ,Journal of Cellular Biochemistry, 2003, 89, pp. 1235-1249.
Liu C. H., et al., Optimization of serum free medium . . . , Biochemical Engineering Journal, 2007, 33, pp. 1-9.
Liu Q. H., et al., Are CD 133 and CD271 Useful in Positive . . . ,Journal of Exp. Hematol., 2010, 18(5), pp. 1286-1291.
International Preliminary Report on Patentability (Chapter 2), International Patent Application No. PCT/JP2013/071559, mailed May 21, 2015, English translation.
Written Opinion of the International Preliminary Examining Authority, PCT/JP2013/071559, mailed Aug. 12, 2014.
Hidekazu Takahasi, et al., "Shortening of Human Cell Life Span by Induction of p16ink4a Through the Platelet-Derived Growth Factor Receptor β," J. Cell. Physiol. (2009), 221, pp. 335-342.
Christian van den Bos, et al., "Human Mesenchymal Stem Cells Respond to Fibroblast Growth Factors," Human Cell vol. 10, No. 1, pp. 45-50 (1997).
Chinese Office Action, CN Patent Application No. 201380033421.8, English translation provided.
Office Action from corresponding KR patent application No. 10-2014-7036218 mailed Dec. 18, 2015.
Park et al.,"Usefulness of Umbilical Cord Blood Cells in Era of Hematopoiesis Research" International Journal of Stem Cells, vol. 2, No. 2 ,2009.
Office Action from corresponding CA patent application No. 2,872,852 mailed Dec. 29, 2015.
Lineage Cell Depletion KitTM, human, Datasheet [online], Miltenyi Biotec GmbH, 2010 [retrieved on Dec. 22, 2015 (Dec. 22, 2015)], from the internet <URL:httb://www.miltenvibiotec.com/en/products-and-services/macs-cell-separation-reagents/hematopoietic-stem-cells/lineage-cell-depletion-kit-human.aspx>.
Mizrahi, K; et al. "Regulatory Functions of TRAIL in Hematopoietic Progenitors: Human Umbilical Cord Blood and Murine Bone Marrow Transplantation". Leukemia (08876924). 24(7), pp. 1325-1334, Jul. 2010 (Jul. 2010).
Lee et al. "Isolation of Multipotent Mesenchymal Stem Cells From Umbilical Cord Blood", Blood. 103(5), pp. 1669-1675, Mar. 2004 (Mar. 2004).
European Search Report of corresponding EP application No. 13833725.8 dated Jan. 7, 2016.
Woodside, S.M. et al. "Fully Automated Magnetic Labeling and Separation of Hematopoietic Cells from Multiple Samples" Blood (ASH Annual Meeting Abstracts), vol. 106, Jan. 1, 2005.
Li Guixin et al., Oncology, Tianjing: Tianjing Science & Technology Publishing House, Mar. 31, 2009, the third paragraph from the bottom on p. 76.
Wang Zhengguo et al., Molecular Traurmatology, Fuzhou: Fujian Science & Technology Publishing House, Aug. 31, 2004, Section 4, lines 1-2 from the bottom of the second paragraph from the bottom on p. 542.
Office Action from corresponding Chinese Patent Application No. 201380033421.8, mailed Aug. 19, 2016.
Office Action for CN 201380033421.8, mailed Jan. 24, 2017.
Office Action for KR patent application No. 10-2014-7036218, mailed Mar. 28, 2017.

\* cited by examiner

METHOD FOR UNDIFFERENTIATED GROWTH OF MESENCHYMAL STEM CELL AND METHOD FOR CONCENTRATION OF MESENCHYMAL STEM CELL

TECHNICAL FIELD

The present invention relates to (i) a method for concentrating cord blood-derived mesenchymal stem cells and then growing the mesenchymal stem cells thus concentrated while maintaining undifferentiated state of the mesenchymal stem cells and (ii) a method for concentrating cord blood-derived mesenchymal stem cells.

BACKGROUND ART

Mesenchymal stem cells are known as cells having differentiation potency to mesenchymal cells (e.g., osteoblasts, adipocytes, myocytes, and chondrocytes). In recent years, it has been reported that mesenchymal stem cells are capable of differentiating them into tissues, such as neurocyte and a liver, which are not developed from mesoblast. As such, great expectations have been placed on the use of the mesenchymal stem cells for regenerative medicine.

Mesenchymal stem cells exist in bone marrow, cord blood, and the like. However, a cell population collected from bone marrow, cord blood, and the like contains an extremely low proportion of mesenchymal stem cells. Under the circumstances, the mesenchymal stem cells are generally concentrated or separated for the utilization thereof. Known as examples of a method for concentration of the mesenchymal stem cells are a HES method, a ficoll method, and a filter method, all of which are methods of removing erythrocytes from blood.

CITATION LIST

Non-Patent Literatures

Non-Patent Literature 1
Pittenger, M. F. et al., Multilineage Potential of Adult Human Mesenchymal Stem Cells. Science, 284:143-147, 1999.
Non-Patent Literature 2
Basford, C. et al., The Cord Blood Separation League Table: a Comparison of the Major Clinical Grade Harvesting Techniques for Cord Blood Stem Cells. Inter. J. Stem Cells, 3:32-45, 2010.
Non-Patent Literature 3
Yasutake, M. et al., Stem cell collection filter system for human placental/umbilical cord blood processing. Vox Sang., 80:101-105, 2001.

SUMMARY OF INVENTION

Technical Problem

By the conventionally known methods, it is impossible to sufficiently concentrate only a trace quantity of mesenchymal stem cells. For example, this gives rise to a problem that even if a concentrated sample of such mesenchymal stem cells, which sample contains a large quantity of foreign matters, is cultured, it is impossible to obtain an adequate number of mesenchymal stem cells.

In view of such a problem, an object of the present invention is to efficiently obtain an adequate number of mesenchymal stem cells from cord blood.

Solution to Problem

In order to solve the above problem, a method in accordance with the present invention is a method for growing mesenchymal stem cells while maintaining undifferentiated state of the mesenchymal stem cells, including the steps of: concentrating cord blood-derived mesenchymal stem cells with use of an antibody that specifically recognizes blood cells, to generate a concentrated sample of cord blood-derived mesenchymal stem cells; and culturing the concentrated sample thus generated in a medium containing SHH, FGF1, or FGF2.

In order to solve the above problem, a method in accordance with the present invention is a method for concentrating mesenchymal stem cells, including the step of: concentrating cord blood-derived mesenchymal stem cells with use of antibody beads that are specifically bound to blood cells.

Advantageous Effects of Invention

According to the present invention, it is possible to efficiently obtain an adequate number of mesenchymal stem cells from cord blood.

DESCRIPTION OF EMBODIMENTS

A method in accordance with the present invention is a method for growing mesenchymal stem cells while maintaining undifferentiated state of the mesenchymal stem cells, including the steps of: generating a concentrated sample of cord blood-derived mesenchymal stem cells with use of an antibody that specifically recognizes blood cells; and culturing the sample thus generated in a medium containing SHH, FGF1, or FGF2.

That is, the method in accordance with the present invention is a method of culturing, with use of a medium containing a particular factor, a sample obtained by removing most of blood cells (erythrocytes and leucocytes) contained in cord blood. As will be shown later in Example, the use of the particular factor allows mesenchymal stem cells to selectively grow while maintaining their undifferentiated state. As such, according to the method in accordance with the present invention, it is possible to obtain mesenchymal stem cells the number of which is just enough that they are applicable to medical uses, from cord blood containing a trace quantity of mesenchymal stem cells.

The following will discuss details of the steps of the method in accordance with the present invention.

[Concentration of Cord Blood-Derived Mesenchymal Stem Cells]

As described previously, the method in accordance with the present invention includes the step of concentrating cord blood-derived mesenchymal stem cells. In this step, the mesenchymal stem cells are concentrated by removing most of blood cells from cord blood with use of an antibody that specifically recognizes a blood cell. This antibody is attached to a carrier such as a magnetic bead. After a carrier being attached to antibodies is mixed with cord blood (a sample derived from cord blood), the carrier being bound to blood cells through the antibodies is collected. This makes it possible to obtain a concentrated sample of mesenchymal stem cells. In an alternative method, the antibody can be labeled by biotin. Such a method utilizes an interaction between biotin with which the antibody is labeled and streptavidin so that blood cells can be selectively removed.

Examples of the antibody include an anti-Glycophorin A antibody, an anti-CD2 antibody, an anti-CD3 antibody, an anti-CD11c antibody, an anti-CD11b antibody, an anti-CD14 antibody, an anti-CD 16 antibody, an anti-CD 19 antibody, an anti-CD24 antibody, an anti-CD56 antibody, an anti-CD61 antibody, an anti-CD66b antibody, and an anti-CD45 antibody. The antibodies listed here are just examples, and various antibodies specifically recognizing erythrocytes or leucocytes and known in this art can be employed in the method in accordance with the present invention.

Taken as an example of the aforementioned method of concentrating mesenchymal stem cells (selectively removing blood cells) with use of an antibody and a carrier, is a method using a combination of a RoboSep™ device and a Negative Selection Progenitor Cell Enrichment kit or the like (both of which are offered by Stem Cell Technologies, Inc.). Such a method allows concentration of cord blood-derived mesenchymal stem cells to be automatically carried out almost without requiring human intervention, and is therefore suitably applied to the method in accordance with the present invention. Stem Cell Technologies, Inc. offers not only the aforementioned kit, but also a kit which allows a combined use of an antibody of user's choice and a reagent. With the combined use of any of the antibodies exemplified above and the kit, it is therefore possible to concentrate cord blood-derived mesenchymal stem cells by means of a RoboSep™ device.

It is preferable that partial separation of cord blood is carried out before the mesenchymal stem cells are concentrated with use of an antibody. It is preferable that cord blood is separated in advance by density gradient centrifugation using a ficoll solution by which monocyte fraction is separated from cord blood.

In the method in accordance with the present invention, it is preferable to determine an approximate number of mesenchymal stem cells contained in a concentrated sample which has been obtained as described above. This makes it possible to determine, in advance, how many days would be required for the growth of the mesenchymal stem cells contained in the concentrated sample to an intended number of cells. The approximate number of mesenchymal stem cells contained in a concentrated sample can be confirmed by FACS analysis using a known flow cytometer and a fluorescently-labeled anti-CD105 antibody or a fluorescently-labeled anti-CD73 antibody. The antibody as used in the FACS analysis needs only to be an antibody specific for a surface marker of a mesenchymal stem cell.

The amount of cord blood obtained from one individual is in the order of about 100 mL. In Japan, cord blood in such an amount (e.g. an amount of approximately 60 mL or larger) that it contains sufficient nucleated cells is stored in a cord blood bank. For this reason, it is difficult to use such cord blood for other applications. As such, it is preferable to obtain an adequate number of mesenchymal stem cells from cord blood in an amount of smaller than 60 mL. As will be demonstrated later in Example, the method in accordance with the present invention allows mesenchymal stem cells that were obtained from 25 mL of cord blood to be grown to over $10^7$ cells in about two weeks.

[Undifferentiated Growth of Mesenchymal Stem Cells]

The method in accordance with the present invention includes the step of culturing a concentrated sample of mesenchymal stem cells. In this step, the sample is cultured in a medium containing, as a growth factor, SHH, FGF1, or FGF2. With use of such a medium, it is possible to grow mesenchymal stem cells, which hardly grow in a medium to which only Flt-3L, IL-3, and IL-6 have been added (see the Example), while maintaining undifferentiated state of the mesenchymal stem cells.

As a basal medium of the aforementioned medium, a known medium used for undifferentiated growth of mesenchymal stem cells is used. The basal medium is (i) the one commercially available from Stem Cell Technologies, Inc. or other supplier as described in the Example below, (ii) the one into which a commercially available medium is partially modified, or (iii) the one having a composition similar to the composition of a commercially available medium. The aforementioned medium can contain known cytokines (e.g. Flt-3L, SCF, IL-3, and IL-6) used for growth of stem cells. Other additives suitably added to the medium are known to a person skilled in the art because they are various additives used for undifferentiated growth of mesenchymal stem cells.

SHH is used in concentrations of, for example, 5 to 500 ng/mL, more preferably 50 to 200 ng/mL, and most preferably 100 ng/mL to be contained in a medium for selectively growing mesenchymal stem cells while maintaining undifferentiated state of the mesenchymal stem cells. FGF1 is used in concentrations of, for example, 0.1 to ng/mL, more preferably 1 to 10 ng/mL, and most preferably 5 ng/mL to be contained in a medium for selectively growing mesenchymal stem cells while maintaining undifferentiated state of the mesenchymal stem cells. FGF2 is used in concentrations of, for example, 0.1 to ng/mL, more preferably 1 to 10 ng/mL, and most preferably 5 ng/mL to be contained in a medium for selectively growing mesenchymal stem cells while maintaining undifferentiated state of the mesenchymal stem cells. Flt-3L is used in concentrations of, for example, 500 to 5000 IU/mL, more preferably 1000 to 4000 IU/mL, and most preferably 2000 IU/mL to be contained in a medium for selectively growing mesenchymal stem cells while maintaining undifferentiated state of the mesenchymal stem cells. SCF is used in concentrations of, for example, 1 to 400 ng/mL, more preferably 10 to 200 ng/mL, and most preferably 100 ng/mL to be contained in a medium for selectively growing mesenchymal stem cells while maintaining undifferentiated state of the mesenchymal stem cells. IL-3 is used in concentrations of, for example, 200 to 5000 IU/mL, more preferably 500 to 2500 IU/mL, and most preferably 1000 IU/mL to be contained in a medium for selectively growing mesenchymal stem cells while maintaining undifferentiated state of the mesenchymal stem cells. IL-6 is used in concentrations of, for example, 200 to 5000 IU/mL, more preferably 500 to 2500 IU/mL, and most preferably 1000 IU/mL to be contained in a medium for selectively growing mesenchymal stem cells while maintaining undifferentiated state of the mesenchymal stem cells.

The concentrated sample is cultured in the medium for an arbitrary length of time period (until an intended number of mesenchymal stem cells are obtained). The length of time period can be changed according to the number of original mesenchymal stem cells contained in an obtained sample. For example, the case where a concentrated sample is collected from 25 mL of cord blood is taken as an example from the Example described later. In this case, the length of time period is about 14 days. By the culturing carried out for about 14 days, the mesenchymal stem cells in the sample can be grown to, for example, approximately over $1 \times 10^7$ cells.

As is apparent from the above descriptions, SHH, FGF1, or FGF2 in accordance with the present invention is an additive (e.g. a growth promoting agent for mesenchymal stem cells) to be added to a medium for selectively growing mesenchymal stem cells having been concentrated from cord blood while maintaining undifferentiated state of the mesenchymal stem cells. Further, the present invention relates to the use of SHH, FGF1, or FGF2 as an additive to be added to a medium for growing mesenchymal stem cells while maintaining undifferentiated state of the mesenchymal stem cells.

In addition, as explained previously, according to a method in accordance with the present invention, it is possible to obtain, from cord blood, an adequate number of mesenchymal stem cells for applications to regenerative medicine and the like field. For example, it is possible to obtain useful mesenchymal stem cells by utilizing a small amount of cord blood (e.g. smaller than 60 mL) which has been used for study purpose.

A method in accordance with the present invention is a method of separating and growing stem cells contained in cord blood which has been extracted from a human. Mesenchymal stem cells obtained in accordance with the present invention are, for example, a material for use in regenerative medicine. Further, mesenchymal stem cells obtained in accordance with the present invention are cells (medical products) directly used in regenerative medicine.

[Overview]

A method in accordance with the present invention is a method for growing mesenchymal stem cells while maintaining undifferentiated state of the mesenchymal stem cells, including the steps of: concentrating cord blood-derived mesenchymal stem cells with use of an antibody that specifically recognizes blood cells, to generate a concentrated sample of cord blood-derived mesenchymal stem cells; and culturing the concentrated sample thus generated in a medium containing SHH, FGF1, or FGF2.

The method in accordance with the present invention is preferably such that the medium further contains SCF.

Further, the method in accordance with the present invention is preferably such that the medium further contains Flt-3L, IL-3, and IL-6.

A method in accordance with the present invention is a method for concentrating mesenchymal stem cells, including the step of: concentrating cord blood-derived mesenchymal stem cells with use of antibody beads that are specifically bound to blood cells.

Further, the method in accordance with the preset invention is preferably such that the antibody beads each comprise a bead and an antibody attached to the bead, and the antibody is selected from the group consisting of an anti-Glycophorin A antibody, an anti-CD2 antibody, an anti-CD3 antibody, an anti-CD11c antibody, an anti-CD11b antibody, an anti-CD14 antibody, an anti-CD16 antibody, an anti-CD 19 antibody, an anti-CD24 antibody, an anti-CD56 antibody, an anti-CD61 antibody, and an anti-CD66b antibody.

EXAMPLE

[1. Concentration of Cord Blood-Derived Mesenchymal Stem Cells]

A monocyte fraction was separated from 25 mL of cord blood by density gradient centrifugation (30 minutes, 900 g, 25° C.) using a ficoll solution (GE Healthcare). Further, blood cells were removed from the monocyte fraction thus obtained by means of a RoboSep™ device (Stem Cell Technologies, Inc.) to obtain a concentrated cell population. The removal of blood cells from the monocyte fraction was carried out by using a Negative Selection Progenitor Cell Enrichment kit (Stem Cell Technologies, Inc.) as a reagent. This reagent contains an anti-Glycophorin A antibody, an anti-CD2 antibody, an anti-CD3 antibody, an anti-CD11c antibody, an anti-CD11b antibody, an anti-CD14 antibody, an anti-CD16 antibody, an anti-CD 19 antibody, an anti-CD24 antibody, an anti-CD56 antibody, an anti-CD61 antibody, and an anti-CD 66b antibody, each of which is attached to magnetic beads. The reagent is therefore capable of removing cells which express antigens recognized by these antibodies on the surface of the cells. A procedure for the removal of blood cells and all the other reagents required for the removal of blood cells followed (i) an operation program for a RoboSep™ device supporting the aforementioned reagent and (ii) a user's manual attached to the RoboSep™ device.

A part of the sample obtained by the above-described operation was mixed with fluorescently-labeled anti-CD 105 antibodies (Biolegend, Inc., antibodies against cell surface markers of mesenchymal stem cells).

Figure 1:
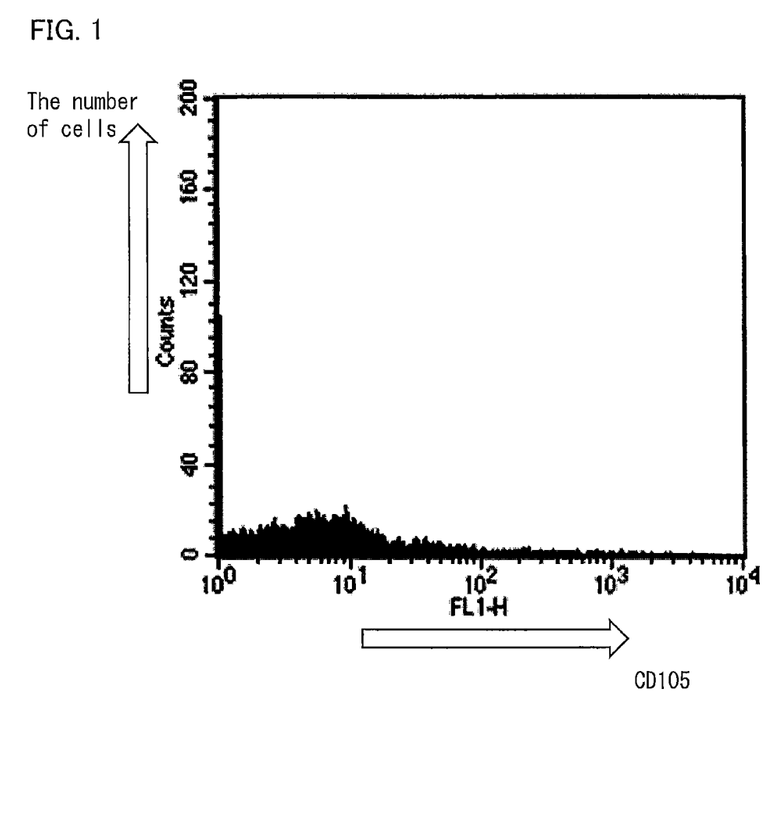
FIG. 1 is a view showing the result of FACS analysis, which was performed to confirm that cells separated from cord blood contained mesenchymal stem cells.

Thereafter, how many mesenchymal stem cells were contained in the mixture thus obtained was examined by means of a BD FACSCalibur® flow cytometer (Japan BD biosciences, Ltd.). The result of such FACS analysis is shown in FIG. 1. FIG. 1 is a view showing a histogram of a single linear region obtained by FACS analysis for CD105 positive cells. As shown in FIG. 1, it was confirmed that the sample contains mesenchymal stem cells that expressed CD 105 on the surfaces thereof.

[2. Undifferentiated Growth of Mesenchymal Stem Cells]

(2-1. Effect of SHH on the Growth of Cord Blood-Derived Cells)

The cells obtained in Section 1 above were grown as follows. For 14 days (starting from the 0th day), the cells were cultured and grown at 37° C. in the presence of 5% $CO_2$ with use of (i) MesenCult-XF Medium (Stem Cell Technologies, Inc.) to which Flt-3L (CellGenix GmbH), SCF (CellGenix GmbH), IL-3 (Miltenyi Biotec K.K.) and IL-6 (Miltenyi Biotec K.K.) and SHH (Miltenyi Biotec K.K.) had been added. Final concentrations of the cytokines added to the medium were as follows: 2000 IU/mL (Flt-3L); 100 ng/mL (SCF); 1000 IU/mL (IL-3); 1000 IU/mL (IL-6); and 100 ng/mL (SHH). In order to confirm the effectiveness of a factor added to the Medium (i), the cells obtained in Section 1 were cultured in (ii) MesenCult-XF Medium to which only Flt-3L, IL-3, and IL-6 were added and in (iii) MesenCult-XF Medium to which no cytokines had been added, in parallel with the above culturing of the cells in the Medium (i). On the 0th day, on the 3rd day, on the 6th day, on the 8th day, on the 11th day, and on the 14th day of the culturing, a total number of cells in each of the Media (i), (ii), and (iii) was determined by trypan blue staining. Time-varying changes in number of cells determined by trypan blue staining is shown in FIG. 2.

Figure 2:
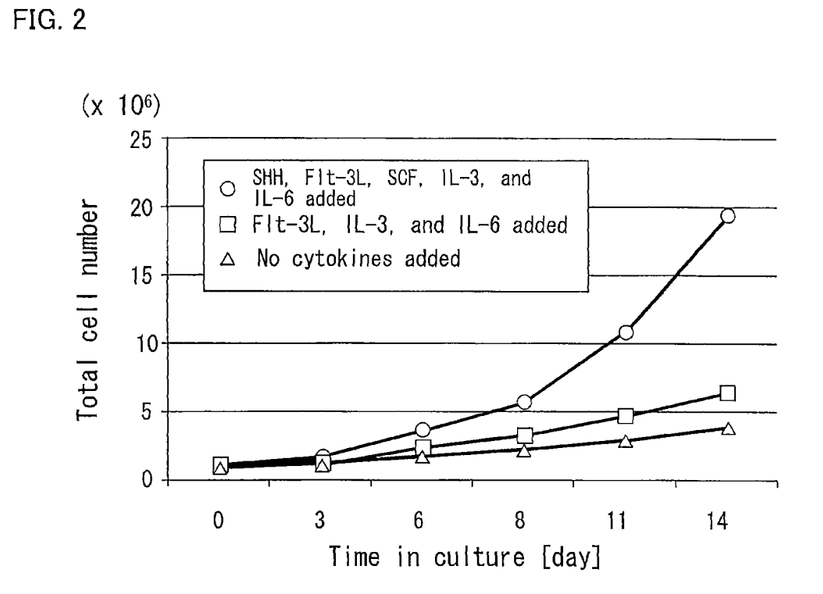
FIG. 2 is a view showing time-varying changes in number of cells grown by a culturing method in accordance with the present invention.

As shown in FIG. 2, it was confirmed that in a case where the medium containing SHH as well as the known cytokines (i.e., the medium containing SHH, Flt-3L, SCF, IL-3, and IL-6) was used for the culturing, $0.9 \times 10^6$ cells on the 0th day had been grown to $1.94 \times 10^7$ cells 14 days after the start of the culturing. On the contrary, the growth of the cells was not substantially confirmed in the medium not containing SHH (the medium to which Flt-3L, IL-3, and IL-6 had been added and the medium to which no cytokines had been added).

(2-2. Confirmation of the Type of Cells Selectively Grown)

Figure 3:
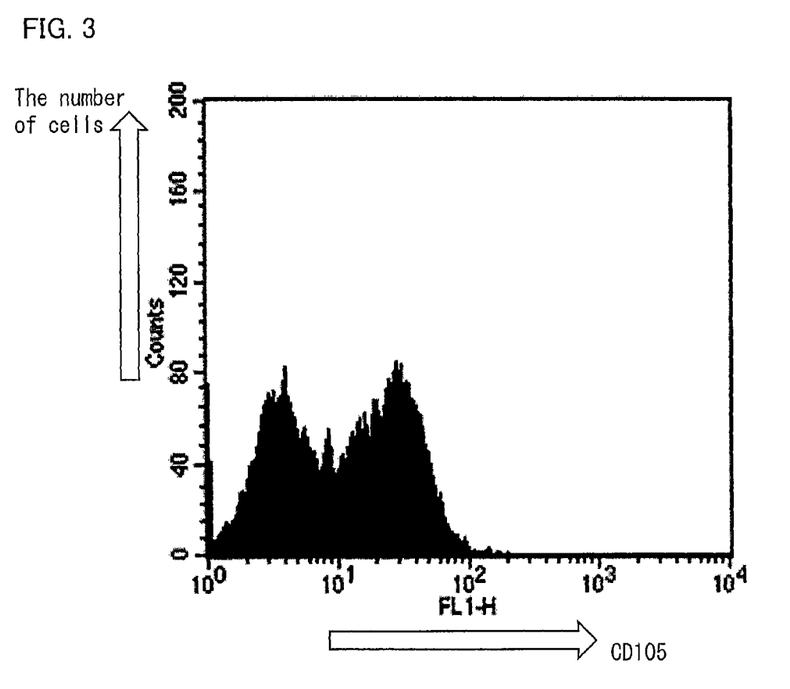
FIG. 3 is a view showing the result of FACS analysis, which was performed on the 14th day of culturing to confirm that mesenchymal stem cells had been selectively grown.
Figure 4:
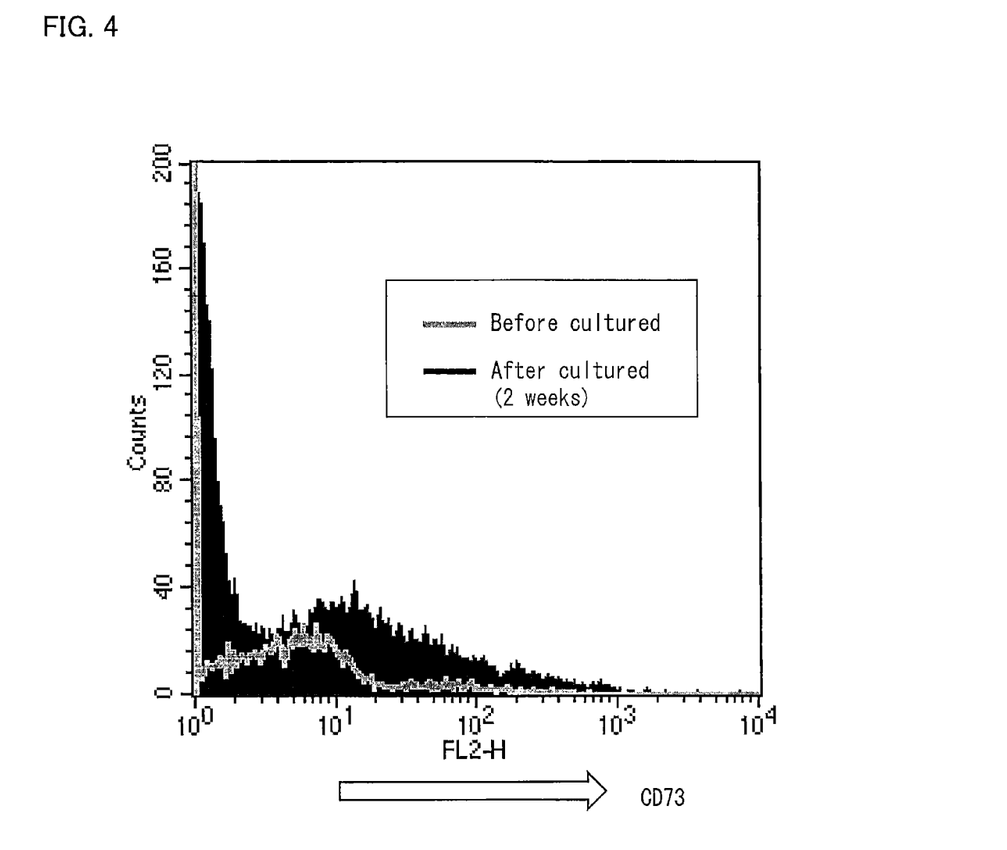
FIG. 4 is a view showing the results of FACS analyses, which were performed to make a comparison between mesenchymal stem cells before cultured and those on the 14th day of culturing in order to confirm that mesenchymal stem cells had been selectively grown.

In order to confirm that the cells grown by the culturing discussed in Section 2-1 were mesenchymal stem cells, the type of the growing cells was determined by FACS analysis on the 14th day of the culturing. A part of cultured cells obtained on the 14th day of the culturing was examined with use of fluorescently-labeled anti-CD105 antibodies (Biolegend, Inc.) and fluorescently-labeled anti-CD73 antibodies (Biolegend, Inc.). All of the FACS analyses were carried out by means of BD FACSCalibur® flow cytometer (Japan BD biosciences, Ltd.). The results of these FACS analyses are shown in FIG. 3 (for the anti-CD105 antibody) and FIG. 4 (for the anti-CD73 antibody). FIG. 3 is a view showing a histogram of a single linear region which was obtained by FACS analysis for CD105 positive cells on the 14th day of the culturing. FIG. 4 is a view showing a histogram of single linear regions which were obtained by FACS analyses for CD73 positive cells before the culturing and on the 14th day of the culturing.

As shown in FIG. 3, the CD105 positive cells (i.e., mesenchymal stem cells) were obviously grown, as compared with the result shown in FIG. 1. Further, as shown in FIG. 4, the CD73 positive cells (i.e., mesenchymal stem cells) were obviously grown by the two-week culturing, as compared with the cells before cultured. The above results show that, in Section 2-1, the mesenchymal stem cells were grown while remaining undifferentiated, and an adequate number of mesenchymal stem cells for applications to, for example, regenerative medicine could be obtained. This revealed that the combination of SHH employed in accordance with the present invention and SCF, in particular, plays an important role in undifferentiated growth of mesenchymal stem cells.

(2-3. Effect of FGF1 or FGF2 on the Growth of Cord Blood-Derived Cells)

The cells obtained in Section 1 above were cultured on a 96-well plate as follows. The cells were grown at 37° C. in the presence of 5% $CO_2$ with use of MesenCult-XF Medium to which cytokines (5 ng/mL of FGF1 (Miltenyi Biotech K.K.), 5 ng/mL of FGF2 (Miltenyi Biotech K.K.), 100 ng/mL of SCF (CellGenix GmbH)) had been added in combination shown below in Table 1. After seven days culturing of the cells, the number of cells was determined under a microscope. From the result of the determination, evaluation was made on how each combined use of cytokines has an effect on the growth of mesenchymal stem cells.

TABLE 1

|  | No cytokines | SCF |
| --- | --- | --- |
| No cytokines | ± | + |
| FGF1 | + | +++ |
| FGF2 | + | +++ |

<Note>

The symbol ± indicates that the growth of cells was not confirmed, the symbol + indicates that the growth of cells was slightly promoted, the symbol ++ indicates that the growth of cells was promoted, and the symbol +++ indicates that the growth of cells was significantly promoted, as compared to the case where no cytokines were added to the MesenCult-XF Medium.

As shown in Table 1, the growth of mesenchymal stem cells was slightly promoted by addition of either FGF1 or FGF2. With a combined use of either FGF1 or FGF2 and SCF, the growth of mesenchymal stem cells was significantly promoted. From the above result, it became clear that FGF1 and FGF2 have an effect of promoting the growth of mesenchymal stem cells.

The present invention is not limited to the aforementioned embodiments and Example and is susceptible of various changes within the scope of the accompanying claims. Also, an embodiment obtained by suitable combinations of various technical means disclosed in the embodiments and Example are included within the technical scope of the present invention.

INDUSTRIAL APPLICABILITY

The present invention is applicable to, in particular, regenerative medicine using mesenchymal stem cells.

The invention claimed is:

1. A method for growing mesenchymal stem cells while maintaining undifferentiated state of the mesenchymal stem cells, comprising the steps of:
    concentrating cord blood-derived mesenchymal stem cells with use of an antibody that specifically recognizes blood cells, to generate a concentrated sample of cord blood-derived mesenchymal stem cells; and
    culturing the concentrated sample thus generated in a medium containing (i) SHH, FGF1, or FGF2 and (ii) SCF.

2. The method according to claim 1, wherein the medium further contains Flt-3L, IL-3, and IL-6.

3. The method as set forth in claim 1, wherein the step of concentrating cord blood-derived mesenchymal stem cells with use of an antibody that specifically recognizes blood cells, to generate a concentrated sample of cord blood-derived mesenchymal stem cells, includes the steps of:
    mixing cord blood and antibody beads that are capable of specifically binding to blood cells; and
    concentrating cord blood-derived mesenchymal stem cells by collecting the antibody beads,
    the antibody beads comprising an anti-Glycophorin A antibody, an anti-CD2 antibody, an anti-CD3 antibody, an anti-CD11 c antibody, an anti-CD11b antibody, an anti-CD14 antibody, an anti-CD16 antibody, an anti-CD19 antibody, an anti-CD24 antibody, an anti-CD56 antibody, an anti-CD61 antibody, and an anti-CD66b antibody.

4. The method as set forth in claim 1, wherein the medium includes (i) SHE or FGF1 and (ii) SCF.

* * * * *

UNITED STATES PATENT AND TRADEMARK OFFICE
CERTIFICATE OF CORRECTION

PATENT NO. : 9,670,461 B2  Page 1 of 1
APPLICATION NO. : 14/342975
DATED : June 6, 2017
INVENTOR(S) : Hiroyuki Abe and Hiroaki Kawasaki It is certified that error appears in the above-identified patent and that said Letters Patent is hereby corrected as shown below:

In the Claims

Column 8, Claim 4, Line 60 reads:
"includes (i) SHE or FGF1 and (ii) SCF."

Whereas it should read:
"includes (i) SHH or FGF1 and (ii) SCF."

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*